(12) United States Patent
Jin et al.

(10) Patent No.: US 11,471,386 B2
(45) Date of Patent: Oct. 18, 2022

(54) NON-SPHERICAL MICROCAPSULE

(71) Applicant: Conopco, Inc., Trumbull, CT (US)

(72) Inventors: Huajin Jin, Shanghai (CN); Xiaoyun Pan, Shanghai (CN)

(73) Assignee: CONOPCO, INC., Englewood Cliffs, NJ (US)

( * ) Notice: Subject to any disclaimer, the term of this patent is extended or adjusted under 35 U.S.C. 154(b) by 74 days.

(21) Appl. No.: 16/770,644

(22) PCT Filed: Dec. 4, 2018

(86) PCT No.: PCT/EP2018/083526
§ 371 (c)(1),
(2) Date: Jun. 8, 2020

(87) PCT Pub. No.: WO2019/129466
PCT Pub. Date: Jul. 4, 2019

(65) Prior Publication Data
US 2021/0169752 A1    Jun. 10, 2021

(30) Foreign Application Priority Data

Dec. 29, 2017  (WO) ................ PCT/CN2017/119799
Feb. 15, 2018  (EP) ..................................... 18156851

(51) Int. Cl.
| | | |
|---|---|---|
| A61K 8/11 | (2006.01) | |
| A61K 8/73 | (2006.01) | |
| A61K 8/84 | (2006.01) | |
| A61Q 13/00 | (2006.01) | |
| B82Y 40/00 | (2011.01) | |

(52) U.S. Cl.
CPC ............... *A61K 8/11* (2013.01); *A61K 8/731* (2013.01); *A61K 8/84* (2013.01); *A61Q 13/00* (2013.01); *A61K 2800/56* (2013.01); *A61K 2800/654* (2013.01); *B82Y 40/00* (2013.01)

(58) Field of Classification Search
None
See application file for complete search history.

(56) References Cited

U.S. PATENT DOCUMENTS

| | | | |
|---|---|---|---|
| 5,051,305 A | 9/1991 | Whitaker, Sr. | |
| 5,691,303 A | 11/1997 | Pan et al. | |
| 6,113,682 A | 9/2000 | Shin et al. | |
| 2004/0180067 A1 | 9/2004 | Popplewell et al. | |
| 2006/0205616 A1 | 9/2006 | Konieczny et al. | |
| 2011/0245141 A1 | 10/2011 | Gizaw et al. | |
| 2012/0128747 A1 | 5/2012 | Veronique et al. | |
| 2013/0018112 A1 | 1/2013 | Thielemans et al. | |
| 2013/0295149 A1 | 11/2013 | Ouali et al. | |
| 2014/0094397 A1 | 4/2014 | Guida et al. | |
| 2014/0206587 A1 | 7/2014 | Chen et al. | |
| 2014/0213499 A1 | 7/2014 | Chen et al. | |
| 2015/0111863 A1 | 4/2015 | Spicer et al. | |
| 2016/0168509 A1 | 6/2016 | Hitchcock et al. | |
| 2016/0256365 A1 | 9/2016 | Dihora et al. | |
| 2017/0049682 A1 | 2/2017 | Bortolai et al. | |
| 2017/0224849 A1 | 8/2017 | Carroll et al. | |
| 2018/0154328 A1 | 6/2018 | Ferguson et al. | |

FOREIGN PATENT DOCUMENTS

| | | | |
|---|---|---|---|
| CN | 1279275 | 1/2001 | |
| CN | 103355656 | 10/2013 | |
| CN | 104959085 | 10/2015 | |
| CN | 108473921 | 8/2018 | |
| DE | 102015225419 | 6/2017 | |
| DE | 102015225429 | 6/2017 | |
| EP | 1512664 | 3/2005 | |
| EP | 2862562 | 4/2015 | |
| GB | 2537777 | 10/2016 | |
| JP | S61282306 | 12/1986 | |
| JP | H06329411 | 11/1994 | |
| JP | 2014169235 | 9/2014 | |
| WO | WO9817710 | 4/1998 | |
| WO | WO9921532 | 5/1999 | |
| WO | WO03055314 | 7/2003 | |
| WO | WO03061607 | 7/2003 | |
| WO | WO2006007393 | 1/2006 | |
| WO | WO2006078841 | 7/2006 | |
| WO | WO2008109462 | 9/2008 | |
| WO | WO2010126742 | 11/2010 | |
| WO | WO2012029643 | 10/2013 | |
| WO | WO2014062867 | 4/2014 | |
| WO | WO2015004045 | 1/2015 | |
| WO | WO2015078552 | 6/2015 | |
| WO | WO2016177607 | 11/2016 | |
| WO | WO-2016177607 A1 * | 11/2016 | ............... A61K 8/73 |
| WO | WO2017107889 | 6/2017 | |
| WO | WO2017134179 | 8/2017 | |
| WO | WO2017175164 | 10/2017 | |
| WO | WO2017178978 | 10/2017 | |
| WO | WO2018189588 | 10/2018 | |

OTHER PUBLICATIONS

Search Report and Written Opinion in EP18156844; dated Apr. 17, 2018.
Search Report and Written Opinion in EP18156851; dated May 30, 2018.
Search Report and Written Opinion in EP18156845; dated Aug. 28, 2018.
Search Report and Written Opinion in EP18173952; dated Nov. 8, 2018.
Search Report and Written Opinion in PCTEP2018082683; dated Jan. 2, 2019.
Search Report and Written Opinion in PCTEP2018083526; dated Jan. 30, 2019.
Search Report and Written Opinion in PCTEP2018084141; dated Mar. 18, 2019.
Search Report and Written Opinion in PCTEP2019056612; dated May 7, 2019.
IPRP2 in PCTEP2018084141; dated Nov. 18, 2019.
IPRP2 in PCTEP2018083526; dated Dec. 11, 2019.
IPRP1 in PCTEP2018082683; dated Jun. 30, 2020.

(Continued)

*Primary Examiner* — Dominic Lazaro
(74) *Attorney, Agent, or Firm* — Krista A. Kostiew

(57) ABSTRACT

Disclosed is a non-spherical microcapsule comprising a core comprising a benefit agent, and a shell comprising nanoparticles having a diameter of 10 to 300 nm and polyurea.

15 Claims, No Drawings

(56) References Cited

OTHER PUBLICATIONS

IPRP2 in PCTEP2019056612; dated Mar. 16, 2020.
Co-pending Application, Jin et al., filed Jun. 8, 2020, U.S. Appl. No. 16/770,667.
Co-pending Application, Jin et al., filed Jun. 8, 2020, U.S. Appl. No. 16/770,656.

* cited by examiner ized. The ingredients in the home care or person care products, for example surfactant, may affect the stability of the microcapsules when the microcapsules are incorporated into the products. Therefore, we developed a non-spherical microcapsule having a shell comprising nanoparticles having a diameter of 10 to 300 nm and polyurea. It was surprisingly found that the such microcapsules are well dispersed and capable of being stable in the presence of surfactant.

NON-SPHERICAL MICROCAPSULE

CROSS REFERENCE TO RELATED APPLICATIONS

The present application is a U.S. National Phase Application under 35 U.S.C. § 371 of International Application No. PCT/EP2018/083526, filed on Dec. 4, 2018, which claims priority to International Application No. PCT/CN2017/119799, filed on Dec. 29, 2017, and European Patent Application No. 18156851.0, filed on Feb. 15, 2018, the contents of which are incorporated herein in their entireties.

FIELD OF THE INVENTION

The present invention is related to microcapsules for delivery of benefit agent. In particular, the present invention relates to a non-spherical microcapsule comprising: (a) a core comprising a benefit agent, and (b) a shell comprising nanoparticles having a diameter of 10 to 300 nm and polyurea.

BACKGROUND OF THE INVENTION

Many home care and personal care products seek to deliver benefit agents to substrates such as textiles, hard surfaces, hair and skin. To achieve a long-lasting benefit agent release performance, encapsulation of the benefit agent in microcapsule has been proposed as a means, in particular for perfume. When applied, the microcapsules may be deposited onto the substrates, for example onto clothes, and broken by action of pressure and/or rubbing when consumers get dressed. The perfume is released and brings superior sensory to the consumers.

US20140206587 A1 (Unilever) discloses a composition comprising a benefit agent delivery particle comprising at least one of hydroxylpropyl methyl cellulose, hydroxylethyl methyl cellulose, hydroxylpropyl guar, hydroxylethyl ethyl cellulose or methyl cellulose. Preferably a non-polysaccharide polymer such as an aminoplast is also present. The benefit agent delivery particle may comprise a perfume. The particles comprising a benefit agent which use certain non-ionic, substituted cellulosic derivates, as above, as a delivery aids, are effective both on cotton and on polyester as well as on hair.

US20140213499 A1 (Unilever) discloses a benefit agent delivery particle comprising dextran as a delivery aid. The deposition system is effective on cotton and polyester and is stable against hydrolysis and enzyme attack.

WO16177607 A1 (Unilever) discloses a microcapsule containing a benefit agent inside a polyurea shell where the polyurea has a nonionic polysaccharide deposition polymer covalently bonded to it. Nonionic deposition polymers are known to provide enhanced deposition onto cellulosic materials for other types of shell material. When attached to polyurea it is found that compared to when attached to prior art microcapsules they provide reduced agglomeration of the microcapsules and an ability for the microcapsules to remain better dispersed in surfactant containing products.

However, there is still much room for improvement from many aspects. One aspect is to improve the efficiency of the deposition of encapsulation microcapsules. Deposition aid is one way to improve the deposition efficiency. The use of deposition aids is however not always desired.

We have recognized that another alternative way to improve the deposition efficiency is to provide a non-spherical microcapsule. However, the microcapsules may aggregate due to the surface interaction of microcapsules when they are prepared. In addition, the ingredients in the home care or person care products, for example surfactant, may affect the stability of the microcapsules when the microcapsules are incorporated into the products. Therefore, we developed a non-spherical microcapsule having a shell comprising nanoparticles having a diameter of 10 to 300 nm and polyurea. It was surprisingly found that the such microcapsules are well dispersed and capable of being stable in the presence of surfactant.

SUMMARY OF THE INVENTION

In a first aspect, the present invention is directed to a non-spherical microcapsule comprising a core comprising a benefit agent, and a shell comprising nanoparticles having a diameter of 10 to 300 nm and polyurea.

In a second aspect, the present invention is directed to a process for preparing the microcapsule of the present composition comprising steps of (a) forming a non-spherical emulsion comprising benefit agent by nanoparticles having a diameter of 10 to 300 nm; and (b) forming a polyurea at the interface of the emulsion.

In a third aspect, the present invention is directed to a home or personal care composition comprising microcapsules of the present invention.

All other aspects of the present invention will more readily become apparent upon considering the detailed description and examples which follow.

DETAILED DESCRIPTION OF THE INVENTION

Except in the examples, or where otherwise explicitly indicated, all numbers in this description indicating amounts of material or conditions of reaction, physical properties of materials and/or use may optionally be understood as modified by the word "about".

All amounts are by weight of the composition, unless otherwise specified.

It should be noted that in specifying any range of values, any particular upper value can be associated with any particular lower value.

For the avoidance of doubt, the word "comprising" is intended to mean "including" but not necessarily "consisting of" or "composed of". In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

"Melting point" refers to the temperature at which it changes from solid to liquid at atmospheric pressure for single compound. "Melting point" refers to slip melting point when it is used for melting point of a mixture. The slip melting point is an index of the temperature at which fat softens and becomes sufficiently fluid to slip in an open capillary tub. The slip melting point may be measured according to AOCS Cc 3-25.

"Diameter" as used herein refers to diameter in non-aggregated state unless otherwise stated. For polydisperse samples having particulate with diameter no greater than 1 μm, diameter means the z-average microcapsule diameter measured, for example, using dynamic light scattering (see international standard ISO 13321) with an instrument such as a Zetasizer Nano™ (Malvern Instruments Ltd, UK). For polydisperse samples having particulate with diameter greater than 1 µm, diameter means the apparent volume median diameter (D50, also known as ×50 or sometimes d(0.5)) of the microcapsules measurable for example, by laser diffraction using a system (such as a Mastersizer™ 2000 available from Malvern Instruments Ltd) meeting the requirements set out in ISO 13320.

"Aspect ratio" as used herein refers to the ratio of the length to width of the microcapsule. Both length and width may be measured by optical microscopy, for example Leica DM2500P. "Length" as used herein refers to the longest measurable distance of the microcapsule in the optical image. "Width" as used herein refers to the longest measurable distance of the microcapsule along the direction perpendicular to the length of the microcapsule in the optical image.

Preferably, the microcapsule is a single core microcapsule. The shape of the microcapsule can be any shape but preferably the microcapsule has rod-like or ellipsoid-like shape. Preferably, the microcapsule has an aspect ratio of 1.3:1 to 20:1, more preferably from 1.4:1 to 10:1, even more preferably from 1.5:1 to 5:1 and still even more preferably from 1.8:1 to 4:1.

The microcapsule has an average length of 0.5 to 100 µm, more preferably from 1 to 65 µm, even more preferably from 3 to 50 µm, still even more preferably from 7 to 35 µm and most preferably from 12 to 25 µm.

Various benefit agents can be incorporated into the microcapsules. The benefit agents may comprise fragrance, pro-fragrance, organic sunscreen, skin lightening agent, anti-aging agent or a mixture thereof. More preferably the benefit agent is selected from fragrance, pro-fragrance, organic sunscreen, skin lightening agent or a mixture thereof.

Even more preferably the benefit agent is fragrance, pro-fragrance or a mixture thereof. Most preferably the benefit agent is fragrance.

Typically, the fragrance comprises components having a boiling point of less than 300, more preferably 100-250 Celsius, measured at one atmosphere. It is also advantageous to comprises components which have a Log P of less than 3.0 (i.e. those which will be partitioned into water).

The pro-fragrance can, for example, be a food lipid. Food lipids typically contain structural units with pronounced hydrophobicity. The majority of lipids are derived from fatty acids. In these 'acyl' lipids the fatty acids are predominantly present as esters and include mono-, di-, triacyl glycerols, phospholipids, glycolipids, diol lipids, waxes, sterol esters and tocopherols.

The fragrance is typically present in an amount of from 10-85% by total weight of the microcapsule, preferably from 15 to 75% by total weight of the microcapsule. The fragrance suitably has a molecular weight of from 50 to 500 Dalton. Pro-fragrances can be of higher molecular weight, being typically 1-10 k Dalton.

The core preferably comprises fatty ester, silicone oil, alkane, or a mixture thereof. More preferably, the core comprises silicone oil, coconut oil, corn oil, cottonseed oil, olive oil, palm oil, soybean oil, peanut oil, pumpkin seed oil, corn oil, sunflower oil, peanut oil, safflower oil, sesame oil, or a mixture thereof. Even more preferably, the core comprises sunflower oil, coconut oil, or a mixture thereof and most preferably the core comprises sunflower oil. It is preferably that the core comprises organic solvent having a melting point of less than 20° C., more preferably less than 0° C. In the event that the fatty ester is a mixture of different fatty esters, the melting point refers to the melting point of the mixture.

The shell comprises nanoparticles having a size of 10 to 300 nm. The nanoparticle may be inorganic nanoparticle such as calcium carbonate, or polymeric particle. It is preferable that the nanoparticle is a polymeric particle. Preferably, the nanoparticle comprises polysaccharide, more preferably cellulose derivative, even more preferably ethyl cellulose and most preferably the nanoparticle is ethyl cellulose nanoparticle. Preferably, the nanoparticle is spherical or quasi-spherical in shape.

The degree of substitution of the ethyl cellulose is preferably 2 to 3, more preferably 2.2 to 2.8. The degree of substitution refers to the average number of the hydroxyl group substituted per anhydroglucose unit (the 'monomer'). The maximum theoretical number of degree of substitution is 3 if all three hydroxyls are replaced.

Suitable polysaccharide (preferably ethyl cellulose) preferably has a dynamic viscosity of 5 to 300 cP at a concentration of 5 wt % in tolune/ethanol (80:20 by weight), more preferably between 30 to 230 cP, and even more preferably 60 to 150 cP at such conditions.

Preferably the diameter of the nanoparticle is 20 to 250 nm. More preferably, the diameter of the nanoparticle is 40 to 200 nm. Even more preferably, the diameter of the nanoparticle is 50 to 160 nm.

Without being bounded to any theory or explanation, the polyurea is believed to form in the gap between the nanoparticles, thus the microcapsule is strengthened to be stable even in the presence of surfactant. The polyurea may be any reaction product of polymerization between at least one polyisocyanate and at least one amine. Preferably, the polyurea is preferably a reaction product of polymerization between at least one polyisocyanate and at least one polyamine having —$NH_2$ and/or —NH groups. Preferably, the weight ratio of the polyisocyanate to the polyamine is from 3:1 to 15:1, more preferably from 1:1 to 5:1, even more preferably from 2:1 to 3:1.

The polyisocyanate preferably comprises, on average, 2 to 4 —N═C═O groups. More preferably, the polyisocyanate comprises two isocyanate functional groups. Preferably the polyisocyanate is water insoluble.

Polyisocyanate may be aliphatic or aromatic but preferably the polyisocyanate comprises aliphatic polyisocyanate. Suitable aliphatic polyisocyanates include hexamethylene diisocyanate (HDI), tetraalkyl xylene diisocyanate, cyclohexane diisocyanate, 1,12-dodecane diisocyanate, 1,4-tetramethylene diisocyanate, 1,3- and 1,4-cyclohexane diisocyanate, 1-isocyanato-3,3,5-trimethyl-5-isocyanatomethylcyclohexane (isophorone diisocyanate), 4,4'-, 2,2'- and 2,4'-dicyclohexyl-methane diisocyanate, or a mixture thereof. More preferably, the polyisocyanate comprises hexamethylene diisocyanate.

Polyamine is preferably a polyalkylene polyamine, preferably containing at least 3 amino groups. More preferably, the polyamines comprise diethylene triamine (DETA), triethylene tetramine (TETA), tetraethylene pentamine (TEPA), pentaethylene hexamine (PEHA), or a mixture thereof. Even more preferably, the polyamine comprises diethylene triamine.

Most preferably, the polyurea is a reaction product of polymerization of hexamethylene diisocyanate and diethylenetriamine.

The weight ratio of the nanoparticle to the benefit agent is preferably from 1:3 to 20:1, more preferably from 1:2 to 12:1 and even more preferably from 1:1.5 to 5:1. The weight ratio of the nanoparticle to the polyurea is preferably from 1:10 to 10:1, more preferably from 1:6 to 6:1 and even more preferably from 1:3 to 3:1.

To further improve the deposition efficiency, it is preferable that the microcapsule further comprises a deposition aid at the outside of the surface. The deposition aid is preferably a polysaccharide. It should be noted that the polysaccharide as deposition aid is chemically different from the polysaccharide which may be comprised in the nanoparticle.

Preferably the polysaccharide is a cellulose, a cellulose derivative, or another ß-1,4-linked polysaccharide having an affinity for cellulose, preferably mannan, glucan, glucomannan, xyloglucan, galactomannan and mixtures thereof. More preferably, the polysaccharide is selected from the group consisting of xyloglucan and galactomannan, cellulose and derivatives thereof. Most preferably, the deposition polymer is selected from locust bean gum, xyloglucan, guar gum or mixtures thereof. Preferably, the polysaccharide has only ß-1,4 linkages in the polymer backbone.

Alternatively or additionally, the polysaccharides may be selected from the group consisting of hydroxyl-propyl cellulose, hydroxy-propyl methyl cellulose, hydroxy-ethyl methyl cellulose, hydroxy-propyl guar, hydroxy-ethyl ethyl cellulose and methyl cellulose.

The preferred molecular weight of the polysaccharide deposition aid is in the range of from about 5 kDa to about 500 kDa, preferably 10 kDa to 500 kDa, more preferably 20 kDa to 300 kDa. Preferably, the deposition aid is present at levels such that the ratio of polymer:microcapsule solids is in the range 1:500 to 3:1, preferably 1:200 to 1:3. The deposition aid is preferably bonded to the shell by means of covalent bond and/or strong adsorption, more preferably by covalent bond.

The microcapsule may be prepared in any suitable process. However, it is preferred that the process comprises:
(a) forming a non-spherical emulsion comprising benefit agent by nanoparticles having a diameter of 10 to 300 nm; and
(b) forming a polyurea at the interface of the emulsion.

Preferably, the process further comprises a step (i) of mixing water, fatty ester, benefit agent, and nanoparticle prior to step (a). To obtain microcapsule having a higher aspect ratio, it is preferable to add a thickener in step (i). Preferably, the thickener comprises gum, starch derivative, cellulose derivatives, carboxyvinyl polymer, or a mixture thereof. More preferably the thickener is a gum. Even more preferably, the thickener is guar gum, locust bean gum, xanthan gum or a mixture thereof. Most preferably, the thickener is locust bean gum.

To form a more stable emulsion, it is preferred to include a cationic polymer in step (i). The cationic polymer is preferably a polyquaternium and more preferably a polyquaternium-7.

The polyurea is formed by polymerizing at least one polyisocyanate and at least one amine. It is preferred that the polyisocyanate is in the oil phase and the amine is in the aqueous phase of the emulsion. It is preferable that step (b) is conducted at −20 to 10° C.

The end-product compositions of the invention may be in any physical form but preferably an aqueous-based liquid. The microcapsule of the invention may be advantageously incorporated into personal care or home care compositions but preferably a personal care composition. The home care composition is preferably an aqueous laundry detergent or an aqueous fabric conditioner. The composition is preferably a skin cleansing composition containing a cleansing surfactant.

Typically, the composition comprises the microcapsules at levels of from 0.001% to 10%, more preferably from 0.005% to 7.55%, more preferably from 0.01 to 5%, and most preferably from 0.1% to 2% by weight of the total composition.

The composition preferably comprises a cleansing surfactant. More than one cleansing surfactant may be included in the composition. The cleaning surfactant may be chosen from soap, non-soap anionic, cationic, non-ionic, amphoteric surfactant and mixtures thereof. Many suitable surface-active compounds are available and are fully described in the literature, for example, in "Surface-Active Agents and Detergents", Volumes I and II, by Schwartz, Perry and Berch. The preferred surface-active compounds that can be used are soaps, non-soap anionic, non-ionic surfactant, amphoteric surfactant or a mixture thereof.

Suitable non-soap anionic surfactants include linear alkylbenzene sulphonate, primary and secondary alkyl sulphates, particularly $C_8$ to $C_{15}$ primary alkyl sulphates; alkyl ether sulphates; olefin sulphonates; alkyl xylene sulphonates; dialkyl sulphosuccinates; fatty acid ester sulphonates; or a mixture thereof. Sodium salts are generally preferred.

Most preferred non-soap anionic surfactant are linear alkylbenzene sulphonate, particularly linear alkylbenzene sulphonates having an alkyl chain length of from $C_8$ to $C_{15}$. It is preferred if the level of linear alkylbenzene sulphonate is from 0 wt % to 30 wt %, more preferably from 1 wt % to 25 wt %, most preferably from 2 wt % to 15 wt %, by weight of the total composition.

Nonionic surfactants that may be used include the primary and secondary alcohol ethoxylates, especially the $C_8$ to $C_{20}$ aliphatic alcohols ethoxylated with an average of from 1 to 20 moles of ethylene oxide per mole of alcohol, and more especially the $C_{10}$ to $C_{15}$ primary and secondary aliphatic alcohols ethoxylated with an average of from 1 to 10 moles of ethylene oxide per mole of alcohol. Non ethoxylated nonionic surfactants include alkylpolyglycosides, glycerol monoethers, and polyhydroxyamides (glucamide). It is preferred if the level of non-ionic surfactant is from 0 wt % to 30 wt %, preferably from 1 wt % to 25 wt %, most preferably from 2 wt % to 15 wt %, by weight of a fully formulated composition comprising the microcapsules of the invention.

Suitable amphoteric surfactants preferably are betaine surfactants. Examples of suitable amphoteric surfactants include, but are not limited to, alkyl betaines, alkylamido betaines, alkyl sulfobetaines, alkyl sultaines and alkylamido sultaines; preferably, those having 8 to about 18 carbons in the alkyl and acyl group. It is preferred that the amount of the amphoteric surfactant is 0 to 20 wt %, more preferably from 1 to 10 wt %, by weight of the composition.

It is also possible to include certain mono-alkyl cationic surfactants. Cationic surfactants that may be used include quaternary ammonium salts of the general formula $R^1R^2R^3R^4N^+X^-$ wherein the R groups are long or short hydrocarbon chains, typically alkyl, hydroxyalkyl or ethoxylated alkyl groups, and X is a counter-ion (for example, compounds in which $R^1$ is a $C_8$-$C_{22}$ alkyl group, preferably a $C_8$-$C_{10}$ or $C_{12}$-$C_{14}$ alkyl group, $R^2$ is a methyl group, and $R^3$ and $R^4$, which may be the same or different, are methyl or hydroxyethyl groups); and cationic esters (for example, choline esters).

Water-soluble skin benefit agents may optionally be formulated into the compositions of the invention. A variety of water-soluble skin benefit agents can be used, and the level can be from 0.1 to 50% but preferably from 1 to 30% by weight of the composition. These materials include, but are not limited to, polyhydroxy alcohols. Preferred watersoluble skin benefit agents are glycerin, sorbitol and polyethylene glycol.

Water-insoluble skin benefit agents may also be formulated into the compositions as conditioners and moisturizers. Examples include silicone oils; hydrocarbons such as liquid paraffins, petrolatum, microcrystalline wax, and mineral oil; and vegetable triglycerides such as sunflowerseed and cottonseed oils.

Some compositions may include thickeners. These may be selected from cellulosics, natural gums and acrylic polymers but not limited by this thickening agent types. Among the cellulosics are sodium carboxymethyl cellulose, hydroxyethyl cellulose, hydroxypropyl methylcellulose and combinations thereof. Suitable gums include xanthan, pectin, karaya, agar, alginate gums and combinations thereof. Among the acrylic thickeners are homopolymers and copolymers of acrylic and methacrylic acids including carbomers such as Carbopol 1382, Carbopol 982, Ultrez, Aqua SF-1 and Aqua SF-2 available from the Lubrizol Corporation. Amounts of thickener may range from 0.01 to 3% by weight of the active polymer (outside of solvent or water) in the compositions.

Preservatives can desirably be incorporated into the compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatabilities between the preservatives and other ingredients. Preservatives are preferably employed in amounts ranging from 0.01% to 2% by weight of the composition.

A variety of other optional materials may be formulated into the compositions. These may include: antimicrobials such as 2-hydroxy-4,2',4'-trichlorodiphenylether (triclosan), 2,6-dimethyl-4-hydroxychlorobenzene, and 3,4,4'-trichlorocarbanilide; scrub and exfoliating particles such as polyethylene and silica or alumina; cooling agents such as menthol; skin calming agents such as aloe vera; and colorants.

In addition, the compositions of the invention may further include 0.5 to 10% by weight of sequestering agents, such as tetra sodium ethylenediaminetetraacetate (EDTA), EHDP or mixtures; opacifiers and pearlizers such as ethylene glycol distearate, titanium dioxide or Lytron 621 (Styrene/Acrylate copolymer); all of which are useful in enhancing the appearance or properties of the product.

Preferably the composition comprises water in an amount of at least 5% by weight of the composition, more preferably at least 25%, even more preferably 40 to 90% and still even more preferably at least 60 to 85% by weight of the composition.

The following examples are provided to facilitate an understanding of the invention. The examples are not intended to limit the scope of the claims.

EXAMPLES

Material

| Chemical Name | Abbreviation | Trade Name | Supplier |
|---|---|---|---|
| Ethyl cellulose | EC | N100 | Hercules |
| Locust Bean Gum | LBG | Grindsted LBG 407 | Danisco |
| Sun flower oil | — | Refined High Oleic Sunflower Seed Oil | Kerry |
| Polyquaternium 7 | PQ-7 | — | Aldrich |
| Hexamethylene Diisocyanate | HDI | — | Energy Chemical |
| Diethylenetriamine | DETA | — | Energy Chemical |
| Pentaerythritol triacrylate | TPTA | — | Aldrich |
| Dithiothreitol | DTT | — | TCI |

Example 1

This example demonstrates the preparation of the microcapsule.

(1) Preparation of Water Dispersion of EC Particles:

10 g of EC powder was dissolved in 1000 mL of acetone under shearing at 700 rpm for 15 minutes, followed by adding 1000 mL of water very quickly and shearing at 700 rpm for another 5 minutes. The acetone and part of water were removed by rotary evaporation to obtain a water dispersion of EC nanoparticle (6 wt %). The diameter of EC nanoparticles is around 130 nm, and zeta potential is around −40 mV, measured by Malvern Zeta sizer Nano ZS 2000 equipment at 25° C.

(2) Preparation of Microcapsules 3.33 g of water dispersion of EC nanoparticle (6 wt %) was mixed with 4 g of water dispersion of LBG (2 wt %) and 12.66 g of deionized water followed by shearing at about 2000 rpm for 3 minutes. 80 µL of water dispersion of PQ-7 (4 wt %), 2 g of sun flower oil containing 100 mg of HDI, and 75 µL of damascone were added into the mixture sequentially. The resultant mixture was homogenized in an ice bath at about 12,000 rpm for 3 minutes. Then, 40 mg of water solution of DETA was added into the mixture dropwise and the mixture was sheared at 300 rpm for 15 minutes at room temperature.

Similar microcapsules were obtained by following similar procedures but with different amount and/or type of monomer as indicated in Table 1. Sample B was prepared in a similar manner without addition of any monomer.

Optical microscopy (DM2500P, Leica, Germany) equipped with a fluorescence light was used to observe the morphology. The states of the microcapsule were described in Table 1. The length (L) and weight (W) were obtained by averaging the values for at least 10 microcapsules (or droplets) in the images. The aspect ratios were calculated by L/W and listed in Table 1.

TABLE 1

| | Monomer 1 | | Monomer 2 | | | |
|---|---|---|---|---|---|---|
| Sample | Abbr. | Amount/mg | Abbr. | Amount/mg | States | Aspect ratio |
| 1 | HDI | 100 | DETA | 40 | Well dispersed | 2.2 |
| 2 | HDI | 200 | DETA | 80 | Well dispersed | 2.5 |

TABLE 1-continued

| Sample | Monomer 1 Abbr. | Amount/ mg | Monomer 2 Abbr. | Amount/ mg | States | Aspect ratio |
|---|---|---|---|---|---|---|
| A | TPTA | 133 | DTT | 103 | Aggregated | 2.0 |
| B | — | — | — | — | Well dispersed | 2.5 |

It was observed that sample 1 and 2 were very well dispersed but sample A aggregated together even if the dispersion was diluted for three times.

Example 2

This example demonstrates the stability of the microcapsule in the presence of surfactant.

Water dispersion of sample 2 (10 wt %) was observed by optical microscopy (Leica DM2500P, Germany). 1 g of water dispersion of sample 2 (10 wt %) was mixed with 1 g of water solution of SLES (26 wt %) by stirring. After 10 minutes, the mixture was observed by optical microscopy. Similar experiments were conducted for sample B to observe the effect of the presence of SLES to the samples.

It was observed that sample 1 was rod in shape. The shape of sample 1 was unchanged even after mixing with SLES solution. In contrast, after mixing with SLES solution, sample B can't be observed in the optical image and it was inferred that sample B was broken.

Example 3

This example demonstrates the deposition efficiency of microcapsules.

TABLE 2

| Ingredient | Wt % |
|---|---|
| Sodium Laureth Sulfate | 12.86 |
| Cocamidopropyl Betaine | 5.67 |
| Cocamide MEA | 1.35 |
| Acrylates Copolymer | 6.00 |
| Tetrasodium EDTA | 0.13 |
| Citric Acid Monohydrate | 0.10 |
| Sodium Hydroxide | 0.20 |
| Polypropylene glycol-400 | 0.70 |
| Sodium Chloride | 0.15 |
| Iodopropynyl Butylcarbamate | 0.07 |
| Phenoxyethanol | 0.60 |
| Sample 2 | 0.20 |
| Water | to 100 |

The deposition efficiency of microcapsule was measured. Formulation I in Table 2 was diluted 10 times and the light absorbance at 600 nm of the diluted formulation I were measured UV-Vis spectrophotometer (Cary 100, available from Agilent Technologies, USA). The value of the absorbance was recorded as $E_0$. Two pieces (5 cm×5 cm) of polycotton were immersed into the diluted formulation I for 20 hours at room temperature. The light absorbance at 600 nm of the remaining diluted formulation I were measured again, and the value was recorded as $E_1$. The deposition efficiency was calculated by following equation of: deposition efficiency=$(E_0-E_1)/E_0\times100\%$. The measurement of deposition efficiency of the microcapsule was repeated at least three times. The deposition efficiency of sample 2 was calculated as 27.2±2.0%.

The invention claimed is:

1. A non-spherical microcapsule comprising:
   a) a core comprising a benefit agent, and
   b) a shell comprising nanoparticles having a diameter of 10 to 300 nm and polyurea;
   wherein the nanoparticles comprise a cellulose derivative and wherein the polyurea is formed in a gap between the nanoparticles.

2. The microcapsule according to claim 1, wherein the benefit agent is a fragrance, pro-fragrance, or a mixture thereof.

3. The microcapsule according to claim 1, wherein the weight ratio of the nanoparticles to the benefit agent is 1:3 to 20:1.

4. The microcapsule according to claim 1, wherein the nanoparticles comprise ethyl cellulose.

5. The microcapsule according to claim 1, wherein the polyurea is reaction product of polymerization of hexamethylene diisocyanate and diethylenetriamine.

6. The microcapsule according to claim 1, wherein the weight ratio of the nanoparticles to the polyurea is 1:10 to 10:1.

7. The microcapsule according to claim 1, wherein the microcapsule has a rod-like or an ellipsoid-like shape.

8. The microcapsule according to claim 1, wherein the microcapsule has an average length of 0.5 to 100 microns.

9. The microcapsule according to claim 8, wherein the average length is 1 to 65 microns.

10. The microcapsule according to claim 1, wherein the microcapsule has an aspect ratio of 1.3:1 to 20:1.

11. The microcapsule according to claim 10, wherein the aspect ratio is 1.5:1 to 5:1.

12. The microcapsule according to claim 1, wherein the benefit agent is a fragrance.

13. A home or personal care composition comprising microcapsules according to claim 1.

14. The home or personal care composition according to claim 13, wherein the composition comprises a cleansing surfactant.

15. A process for preparing a non-spherical microcapsule according to claim 1, comprising the steps of:
   a) forming a non-spherical emulsion comprising benefit agent by nanoparticles having a diameter of 10 to 300 nm; and
   b) forming a polyurea at the interface of the emulsion, thereby forming the non-spherical microcapsule.

* * * * *